(12) United States Patent
Gross et al.

(10) Patent No.: US 11,583,695 B2
(45) Date of Patent: *Feb. 21, 2023

(54) SYSTEMS AND METHODS FOR PHOTOTHERAPY

(71) Applicant: Zerigo Health, Inc., San Diego, CA (US)

(72) Inventors: Martyn C. Gross, San Diego, CA (US); Remo Moomiaie, Dover, DE (US); Andre S. Gamelin, Vista, CA (US)

(73) Assignee: Zerigo Health, Inc., San Diego, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/166,872

(22) Filed: Feb. 3, 2021

(65) Prior Publication Data
US 2021/0178181 A1 Jun. 17, 2021

Related U.S. Application Data

(63) Continuation of application No. 15/881,422, filed on Jan. 26, 2018, now abandoned, which is a (Continued)

(51) Int. Cl.
*A61N 5/06* (2006.01)

(52) U.S. Cl.
CPC .... *A61N 5/0616* (2013.01); *A61N 2005/0626* (2013.01); *A61N 2005/0627* (2013.01);
(Continued)

(58) Field of Classification Search
CPC .......... A61N 5/0616; A61N 2005/0627; A61N 2005/0651; A61N 2005/0661; A61N 2005/0626; A61B 5/4836
See application file for complete search history.

(56) References Cited

U.S. PATENT DOCUMENTS 5,698,866 A 12/1997 Doiron et al.
5,720,772 A 2/1998 Eckhouse
(Continued)

FOREIGN PATENT DOCUMENTS

CA 2387071 A1 2/2002
CA 2452408 A1 1/2003
(Continued)

OTHER PUBLICATIONS

Asztalos et al., The impact of emollients on phototherapy: A review. Journal of the American Academy of Dermatology, 68(5):817-824, 2013.
(Continued)

*Primary Examiner* — Nathan J Jenness
(74) *Attorney, Agent, or Firm* — Wilson Sonsini Goodrich & Rosati

(57) ABSTRACT

The present disclosure relates to systems, methods, and uses of systems for treating a skin condition with phototherapy. A system comprises (a) a phototherapy device comprising a phototherapy light source; (b) a patient computing device comprising a processor and a memory, the patient computing device configured to: transmit a first signal to the phototherapy device enabling operation of the phototherapy device according to one or more conditional prescription parameters, activate the phototherapy light source, and transmit a second signal reporting operation of the phototherapy device; and (c) a server configured to communicate with the patient computing device and receive the second signal.

15 Claims, 1 Drawing Sheet

Related U.S. Application Data continuation of application No. 14/613,297, filed on Feb. 3, 2015, now Pat. No. 9,913,993.

(60) Provisional application No. 61/935,136, filed on Feb. 3, 2014.

(52) U.S. Cl.
CPC ............... *A61N 2005/0651* (2013.01); *A61N 2005/0661* (2013.01)

(56) References Cited

U.S. PATENT DOCUMENTS

| | | | |
|---|---|---|---|
| 5,836,999 | A | 11/1998 | Eckhouse et al. |
| 6,063,108 | A | 5/2000 | Salansky et al. |
| 6,290,713 | B1 | 9/2001 | Russell |
| 6,413,268 | B1 | 7/2002 | Hartman |
| 6,436,127 | B1 | 8/2002 | Anderson et al. |
| 6,663,659 | B2 | 12/2003 | McDaniel |
| 6,692,251 | B1 | 2/2004 | Logan et al. |
| 6,835,202 | B2 | 12/2004 | Harth et al. |
| 6,902,563 | B2 | 6/2005 | Wilkens et al. |
| 7,081,128 | B2 | 7/2006 | Hart et al. |
| 7,087,074 | B2 | 8/2006 | Hasegawa |
| 7,211,299 | B2 | 5/2007 | Siegel |
| 7,252,628 | B2 | 8/2007 | Van Hal et al. |
| 7,276,059 | B2 | 10/2007 | Irwin |
| H2242 | H | 7/2010 | Gonzales |
| 7,886,749 | B2 | 2/2011 | Irwin |
| 7,887,533 | B2 | 2/2011 | Barolet et al. |
| 7,921,853 | B2 | 4/2011 | Fiset |
| 7,985,219 | B2 | 7/2011 | Wilkens et al. |
| 8,157,807 | B2 | 4/2012 | Ferren et al. |
| 8,435,273 | B2 | 5/2013 | Lum et al. |
| 8,486,056 | B2 | 7/2013 | Irwin |
| 8,486,124 | B2 | 7/2013 | Hendrix et al. |
| 8,518,027 | B2 | 8/2013 | Weckwerth et al. |
| 8,518,094 | B2 | 8/2013 | Wang |
| 8,523,849 | B2 | 9/2013 | Liu et al. |
| 8,620,451 | B2 | 12/2013 | Kennedy |
| 8,801,254 | B2 | 8/2014 | McNeill et al. |
| 8,864,362 | B2 | 10/2014 | Sherman et al. |
| 9,901,747 | B2 | 2/2018 | Gamelin et al. |
| 9,913,993 | B2 | 3/2018 | Gross et al. |
| 2002/0022008 | A1 | 2/2002 | Forest et al. |
| 2002/0128695 | A1 | 9/2002 | Harth et al. |
| 2002/0182563 | A1 | 12/2002 | Boutoussov et al. |
| 2004/0054386 | A1 | 3/2004 | Martin et al. |
| 2004/0166249 | A1 | 8/2004 | Siegel |
| 2004/0188696 | A1 | 9/2004 | Hsing et al. |
| 2005/0143793 | A1 | 6/2005 | Korman et al. |
| 2005/0157515 | A1 | 7/2005 | Chen et al. |
| 2005/0177208 | A1 | 8/2005 | Irwin |
| 2005/0196720 | A1 | 9/2005 | Ostler et al. |
| 2005/0206518 | A1 | 9/2005 | Welch et al. |
| 2006/0085053 | A1 | 4/2006 | Anderson et al. |
| 2006/0106435 | A1 | 5/2006 | Fraval |
| 2006/0289887 | A1 | 12/2006 | Bui et al. |
| 2007/0049996 | A1 | 3/2007 | Black |
| 2007/0078501 | A1 | 4/2007 | Altshuler et al. |
| 2007/0198004 | A1 | 8/2007 | Altshuler et al. |
| 2007/0276455 | A1 | 11/2007 | Fiset |
| 2008/0027518 | A1 | 1/2008 | Island et al. |
| 2009/0221999 | A1 | 9/2009 | Shahidi |
| 2009/0240310 | A1 | 9/2009 | Kennedy |
| 2009/0254154 | A1 | 10/2009 | De Taboada et al. |
| 2010/0069898 | A1 | 3/2010 | O'Neil et al. |
| 2010/0076529 | A1 | 3/2010 | Tucker et al. |
| 2010/0127299 | A1 | 5/2010 | Smith et al. |
| 2010/0145419 | A1 | 6/2010 | Fraval |
| 2010/0196343 | A1 | 8/2010 | O'Neil et al. |
| 2011/0034971 | A1 | 2/2011 | Svanberg et al. |
| 2011/0037002 | A1 | 2/2011 | Johnson et al. |
| 2011/0037844 | A1 | 2/2011 | Johnson et al. |
| 2011/0125229 | A1 | 5/2011 | Lytle et al. |
| 2011/0144410 | A1 | 6/2011 | Kennedy |
| 2011/0190579 | A1 | 8/2011 | Ziarno et al. |
| 2012/0022618 | A1 | 1/2012 | Lum et al. |
| 2012/0059441 | A1 | 3/2012 | Chang et al. |
| 2012/0065493 | A1 | 3/2012 | Gertner |
| 2012/0078329 | A1 | 3/2012 | Shimada |
| 2012/0116485 | A1 | 5/2012 | Burgmann |
| 2012/0165907 | A1 | 6/2012 | Wagenaar et al. |
| 2012/0191162 | A1 | 7/2012 | Villa |
| 2012/0212960 | A1 | 8/2012 | Rodriguez |
| 2012/0222618 | A1 | 9/2012 | Olsen et al. |
| 2012/0283711 | A1 | 11/2012 | Liu et al. |
| 2013/0013032 | A1 | 1/2013 | Irwin |
| 2013/0030264 | A1 | 1/2013 | Gopalakrishnan et al. |
| 2013/0066404 | A1 | 3/2013 | Tapper et al. |
| 2013/0115180 | A1 | 5/2013 | Goren et al. |
| 2013/0144364 | A1 | 6/2013 | Wagenaar et al. |
| 2013/0172963 | A1 | 7/2013 | Moffat |
| 2013/0190841 | A1 | 7/2013 | McMillan |
| 2013/0231720 | A1 | 9/2013 | Luellau |
| 2013/0245417 | A1 | 9/2013 | Spector |
| 2013/0245724 | A1 | 9/2013 | Kaufman |
| 2013/0282080 | A1 | 10/2013 | Hendrix et al. |
| 2013/0301034 | A1 | 11/2013 | Olds et al. |
| 2013/0317574 | A1 | 11/2013 | Gourgouliatos et al. |
| 2013/0345687 | A1 | 12/2013 | McMillan et al. |
| 2014/0031906 | A1 | 1/2014 | Brezinski |
| 2014/0039473 | A1 | 2/2014 | Liu et al. |
| 2014/0052223 | A1 | 2/2014 | Toepfer |
| 2014/0157174 | A1 | 6/2014 | Deroberts |
| 2014/0194957 | A1 | 7/2014 | Rubinfeld et al. |
| 2014/0244292 | A1 | 8/2014 | Rosenberg et al. |
| 2014/0277299 | A1 | 9/2014 | Intintoli et al. |
| 2014/0288351 | A1 | 9/2014 | Jones |
| 2014/0303547 | A1 | 10/2014 | Loupis et al. |
| 2015/0022093 | A1 | 1/2015 | Smith et al. |
| 2015/0025601 | A1 | 1/2015 | Fiset |
| 2015/0025602 | A1 | 1/2015 | Wagenaar et al. |
| 2015/0070188 | A1 | 3/2015 | Aramburu |
| 2015/0148871 | A1 | 5/2015 | Maxik et al. |
| 2015/0165229 | A1 | 6/2015 | Rodrigues |
| 2015/0174361 | A1 | 6/2015 | Baaijens et al. |
| 2015/0177059 | A1 | 6/2015 | Lian et al. |
| 2015/0217130 | A1 | 8/2015 | Gross et al. |
| 2015/0230863 | A1 | 8/2015 | Youngquist et al. |
| 2017/0056686 | A1 | 3/2017 | Gamelin et al. |
| 2021/0187317 | A1 | 6/2021 | Gamelin et al. |

FOREIGN PATENT DOCUMENTS

| | | |
|---|---|---|
| CA | 2767594 A1 | 1/2011 |
| CA | 2861620 A1 | 7/2013 |
| CN | 1578688 A | 2/2005 |
| CN | 1728971 A | 2/2006 |
| CN | 1250302 C | 4/2006 |
| CN | 102006833 A | 4/2011 |
| CN | 102470252 A | 5/2012 |
| CN | 102481456 A | 5/2012 |
| CN | 102811766 A | 12/2012 |
| CN | 102870020 A | 1/2013 |
| CN | 104168953 A | 11/2014 |
| CN | 104640602 A | 5/2015 |
| EP | 1307261 A1 | 5/2003 |
| EP | 1575436 A1 | 9/2005 |
| EP | 2252229 A1 | 11/2010 |
| EP | 2258301 A2 | 12/2010 |
| EP | 2445586 A1 | 5/2012 |
| EP | 2448635 A2 | 5/2012 |
| EP | 2451528 A1 | 5/2012 |
| EP | 2494389 A2 | 9/2012 |
| EP | 2670334 A1 | 12/2013 |
| EP | 2800605 A1 | 11/2014 |
| EP | 2877243 A1 | 6/2015 |
| EP | 3280342 A1 | 2/2018 |
| JP | 2002514481 A | 5/2002 |
| JP | 2005534201 A | 11/2005 |
| JP | 2006252506 A | 9/2006 |
| JP | 2007510466 A | 4/2007 |
| JP | 2008528188 A | 7/2008 |

(56) References Cited

FOREIGN PATENT DOCUMENTS

| | | | |
|---|---|---|---|
| JP | 2008539808 | A | 11/2008 |
| JP | 2009532079 | A | 9/2009 |
| JP | 2012502696 | A | 2/2012 |
| JP | 2012090950 | A | 5/2012 |
| JP | 2012531938 | A | 12/2012 |
| KR | 101349157 | B1 | 1/2014 |
| WO | WO-9958195 | A1 | 11/1999 |
| WO | WO-0114012 | A1 | 3/2001 |
| WO | WO-0213905 | A1 | 2/2002 |
| WO | WO-03001984 | A2 | 1/2003 |
| WO | WO-2004011848 | A2 | 2/2004 |
| WO | WO-2004054458 | A1 | 7/2004 |
| WO | WO-2005046793 | A2 | 5/2005 |
| WO | WO-2006081312 | A2 | 8/2006 |
| WO | WO-2006099413 | A2 | 9/2006 |
| WO | WO-2008061197 | A2 | 5/2008 |
| WO | WO-2009113986 | A1 | 9/2009 |
| WO | WO-2010010321 | A1 | 1/2010 |
| WO | WO-2010033630 | A1 | 3/2010 |
| WO | WO-2010150165 | A1 | 12/2010 |
| WO | WO-2011001344 | A2 | 1/2011 |
| WO | WO-2011004170 | A1 | 1/2011 |
| WO | WO-2011053804 | A2 | 5/2011 |
| WO | WO-2011089540 | A1 | 7/2011 |
| WO | WO-2011109628 | A1 | 9/2011 |
| WO | WO-2012106689 | A1 | 8/2012 |
| WO | WO-2013020179 | A1 | 2/2013 |
| WO | WO-2013103743 | A1 | 7/2013 |
| WO | WO-2013138517 | A1 | 9/2013 |
| WO | WO-2014013386 | A1 | 1/2014 |
| WO | WO-2014018103 | A1 | 1/2014 |
| WO | WO-2014040177 | A1 | 3/2014 |
| WO | WO-2014054458 | A1 | 4/2014 |
| WO | WO-2014076503 | A1 | 5/2014 |
| WO | WO-2014131115 | A1 | 9/2014 |
| WO | WO-2014162271 | A2 | 10/2014 |
| WO | WO-2015041919 | A1 | 3/2015 |
| WO | WO-2015117159 | A1 | 8/2015 |
| WO | WO-2016164228 | A1 | 10/2016 |
| WO | WO-2017019455 | A2 | 2/2017 |

OTHER PUBLICATIONS

Australian Application No. 2020281033 Examination Report No. 1 dated Aug. 3, 2021.
Canadian Patent Application No. 2,980,541 Office Action dated Jan. 4, 2022.
European Patent Application No. 15743284.0 extended European Search Report dated Septembers, 2017.
European Patent Application No. 15743284.0 Office Action dated Jun. 13, 2018.
European Patent Application No. 15831098.5 European Search Report dated Mar. 4, 2019.
European Patent Application No. 20187070.6 European Search Report dated Jan. 26, 2021.
Japanese Application No. 2021-055671 Reason for Refusal dated Jan. 24, 2022.
Japanese Patent Application No. 2016-567480 First office Action dated Apr. 2, 2018.
Japanese Patent Application No. 2017-548298 Office Action dated Mar. 23, 2020.
PCT Patent Application No. PCT/US2016/024996 International Preliminary Report on Patentability dated Oct. 10, 2017.
PCT Patent Application No. PCT/US2016/024996 International Search Report and Written Opinion dated Jul. 1, 2016.
PCT/US2015/014327 International Preliminary Report on Patentability dated Mar. 31, 2016.
PCT/US2015/014327 International Search Report and Written Opinion dated May 7, 2015.
PCT/US2016/043378 International Search Report and Written Opinion dated Jan. 26, 2017.
U.S. Appl. No. 15/747,100 Final Office Action dated Mar. 10, 2022.
U.S. Appl. No. 14/613,297 Office Action dated Feb. 8, 2017.
U.S. Appl. No. 14/613,297 Office Action dated Jul. 11, 2017.
U.S. Appl. No. 14/613,297 Office Action dated Nov. 6, 2017.
U.S. Appl. No. 15/351,119 Office Action dated Aug. 28, 2017.
U.S. Appl. No. 15/351,119 Office Action dated Feb. 23, 2017.
U.S. Appl. No. 15/747,100 Final Office Action dated Jan. 28, 2021.
U.S. Appl. No. 15/747,100 Office Action dated Apr. 30, 2020.
U.S. Appl. No. 15/747,100 Office Action dated Oct. 14, 2021.
U.S. Appl. No. 15/747,100 Restriction Requirement dated Dec. 16, 2019.
U.S. Appl. No. 15/839,678 Office Action dated Apr. 1, 2019.
U.S. Appl. No. 15/839,678 Office Action dated Dec. 31, 2019.
U.S. Appl. No. 15/839,678 Office Action dated Sep. 4, 2020.
U.S. Appl. No. 15/881,422 Final Office Action dated Aug. 4, 2020.
U.S. Appl. No. 15/881,422 Office Action dated Jan. 16, 2020.
Yarbrough et al., Continued use of home narrowband ultraviolet B light phototherapy for psoriasis after completion of a clinical trial. Journal of American Academy of Dermatology, 60(5): 877-879, 2009.

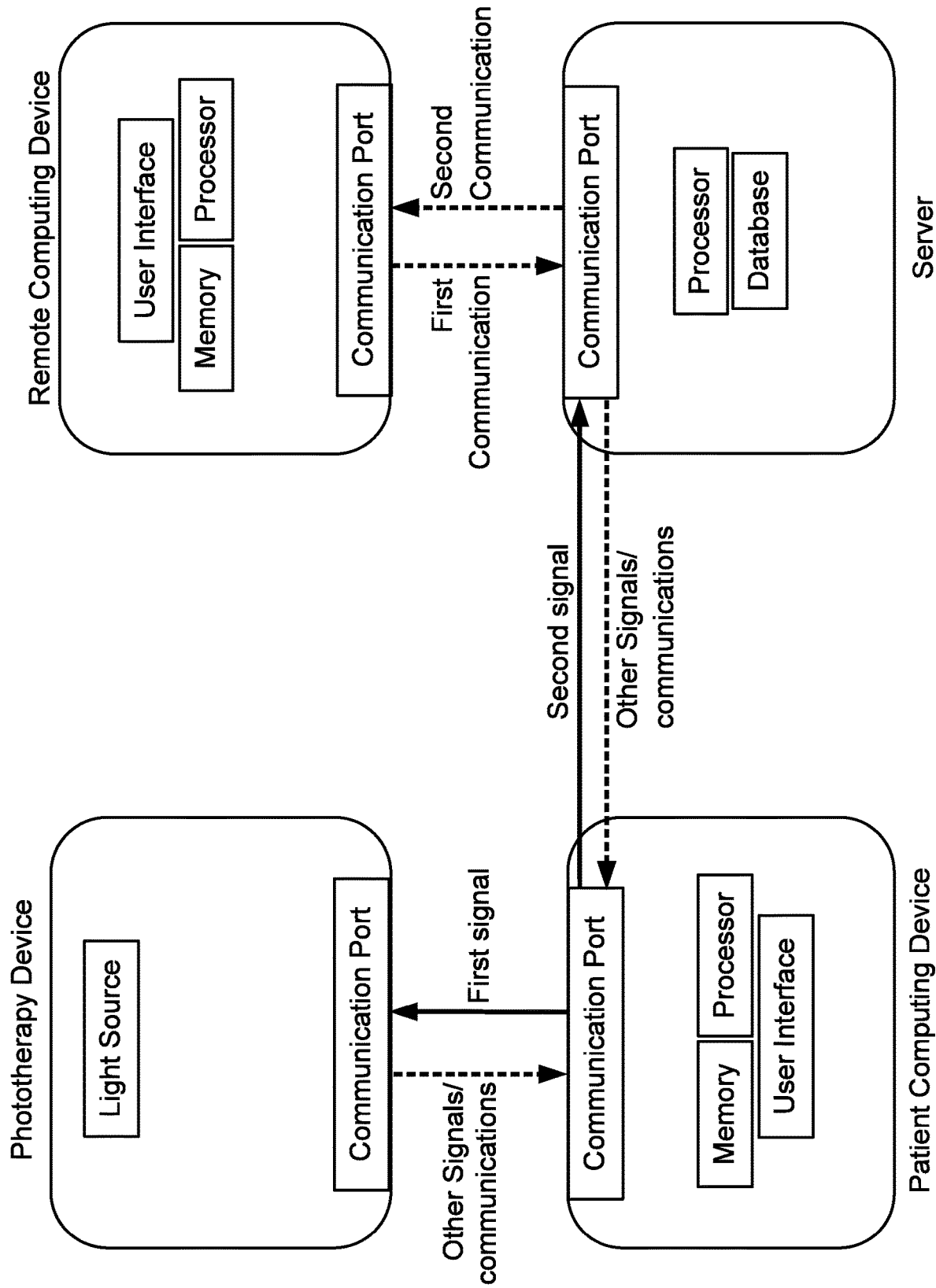

SYSTEMS AND METHODS FOR PHOTOTHERAPY

CROSS REFERENCE

This application is a continuation of U.S. patent application Ser. No. 15/881,422, filed Jan. 26, 2018, which is a continuation of U.S. patent application Ser. No. 14/613,297, filed Feb. 3, 2015, now U.S. Pat. No. 9,913,993, issued Mar. 13, 2018, entitled "SYSTEMS AND METHODS FOR PHOTOTHERAPY", which claims the benefit of U.S. Provisional Application No. 61/935,136, filed Feb. 3, 2014, the contents of which is hereby incorporated by reference in its entirety.

BACKGROUND

Psoriasis is a common relapsing remitting skin condition that affects roughly 2-4% of the general population. Psoriasis is characterized by red, scaly, itchy skin lesions that may occur anywhere on the body. The causes of psoriasis are not well understood, but it is generally believed to be a genetic disease.

The general pathogenesis psoriasis is immune mediated. Immune cells incorrectly identify normal skin cells as pathogenic, and send out cell signals that cause the production of new skin cells. The overgrown skin cells comprise the psoriasis lesions.

No cure currently exists for psoriasis, and it is difficult to treat in part because of its chronically recurring and remitting nature.

Vitiligo is a skin condition in which there is a loss of brown color (pigment) from areas of skin, resulting in irregular white patches that feel like normal skin.

Eczema is a term for several different types of skin swelling.

SUMMARY

In a first broad embodiment, the present disclosure provides a system for treating a skin condition with phototherapy. The system includes a phototherapy device comprising a phototherapy light source and a patient computing device comprising a processor and a memory. The patient computing device is configured to: transmit a first signal to the phototherapy device enabling operation of the phototherapy device according to one or more conditional prescription parameters, activate the phototherapy light source, and transmit a second signal reporting operation of the phototherapy device. The system also includes a server configured to communicate with the patient computing device and receive the second signal.

In some embodiments, the system also includes a remote computing device configured to communicate with the server, the remote computing device including a processor and a memory, the remote computing device being configured to present a graphic user interface allowing a health care provider to set the one or more conditional prescription parameters, review information pertaining to operation of the phototherapy device, and adjust the one or more conditional prescription parameters, transmit a first communication to the server, and receive a second communication from the server.

In some embodiments, the conditional prescription parameters include one or more of: number and location of treatment sites, initial dose, method to determine subsequent doses, method to determine adjustments for missed days, maintenance treatment dose, treatment assessment method, treatment assessment frequency, treatment parameters in case the patient computing device is unavailable, enablement of the treatment dependent on completion of office visits or consults, enablement of the device dependent on acknowledgement of physician supplied materials, enablement of the device dependent on fulfillment of other physician requests such as user supplied photos, conditions in which the treatment would be disabled, or combinations thereof.

In some embodiments, the server comprises a database of patient records and prescribed treatment protocols comprising conditional prescription parameters.

In some embodiments, the patient records comprise: treatment dates and times, treatment durations, applied treatment energies, treatment site photos, analysis of treatments site photos, patient/physician correspondence, assessments of treatment sites, changes to the treatment protocol, and/or a combination thereof.

In some embodiments, the server is configured to perform analysis of patient records, prescribed treatment protocols, and outcomes over populations of patients.

In some embodiments, the server is further configured to perform computational analysis. In some embodiments, the computational analysis comprises an analysis of degree of erythema of a treated area of skin and surrounding skin tissue. In some embodiments, the computational analysis comprises an analysis of treatment progression comprising size and severity of the skin condition or of a disease.

In an embodiment, the server is further configured to determine an initial phototherapy dose based on a user skin type or susceptibility to erythema of a user of the phototherapy device.

In an embodiment, the phototherapy device comprises a hand-held phototherapy device. In some embodiments, the phototherapy light source is configured to emit a light comprising a UVB wavelength in the range of 300-320 nm. In some embodiments, the phototherapy light source comprises a light emitting diode (LED).

In some embodiments, the patient computing device comprises a smartphone, the signals comprise wireless signals, the transmitter comprises a wireless transmitter, and the receiver comprises a wireless receiver.

In some embodiments, the patient computing device is further configured to present an interface allowing the patient to capture an image of a treated area of skin and the surrounding skin tissue. In some embodiments, the patient computing device is further configured to present an interface providing guidance to the patient for operation of the phototherapy device. In some embodiments, the patient computing device is further configured to present an interface providing a treatment schedule, treatment reminders, directions for how to use the phototherapy device, or any combination thereof.

In some embodiments, the skin condition comprises psoriasis, vitiligo, or eczema.

In a second broad embodiment, the present disclosure provides use of the phototherapy system(s) as described herein for treating a skin condition with phototherapy.

In a third broad embodiment, the present disclosure provides a method for treating a skin condition with phototherapy, including: transmitting, by a patient computing device, a first signal to a phototherapy device comprising a phototherapy light source, the first signal enabling operation of the phototherapy device according to one or more conditional prescription parameters; activating, by the patient computing device, the phototherapy light source; transmitting, by the patient computing device, a second signal; and receiving, by a server, the second signal, the server being configured to communicate with the patient computing device.

In some embodiments, the method includes transmitting, by a remote computing device, a first communication to the server; and receiving, by the remote computing device, a second communication from the server.

In some embodiments, the method includes further comprising transmitting the first communication from the server to the patient computing device and receiving by the patient computing device the first communication. In some embodiments, the first communication enables the patient computing device to transmit the first signal.

In some embodiments, the server stores patient records. In some embodiments, the patient records comprise: treatment dates and times, treatment durations, applied treatment energies, treatment site photos, analysis of treatments site photos, patient/physician correspondence, assessments of treatment sites, changes to the treatment protocol, or any combination thereof.

In some embodiments, the methods include performing, by the server, image analysis of an image of an area of skin affected by a skin condition and/or surrounding skin tissue. In some embodiments, the image analysis comprises an analysis of degree of erythema of an area of skin affected by the skin condition and/or the surrounding skin tissue. In some embodiments, the image analysis comprises an analysis of treatment progression comprising size and severity of disease.

In some embodiments, the method comprises a step of determining, by the server, a subsequent phototherapy dose based on a skin type or susceptibility to erythema of a user of the phototherapy device.

In some embodiments, the phototherapy device comprises a hand-held phototherapy device. In some embodiments, the phototherapy light source is configured to emit a light comprising a UVB wavelength in the range of 300-320 nm. In some embodiments, the phototherapy light source comprises a light emitting diode (LED).

In some embodiments, the patient computing device comprises a smartphone and the signals comprise wireless signals.

In some embodiments, the method further comprises displaying, by the patient computing device, a treatment schedule, treatment reminders, directions for how to use the phototherapy device, or any combination thereof.

In some embodiments, the skin condition comprises psoriasis, eczema, or vitiligo.

In a fourth broad embodiment, the present disclosure provides a system for treating a skin condition, the condition comprising psoriasis, vitiligo, or eczema, with phototherapy, the system comprising a hand-held phototherapy device comprising a light emitting diode (LED) phototherapy light source configured to emit a light comprising a UVB wavelength in the range of 300-320 nm and a signal receiver; and a patient computing device comprising a smartphone, the smartphone comprising a processor and a memory, the smartphone configured to: present an interface providing a treatment schedule, treatment reminders, and directions for how to use the phototherapy device; transmit a first signal to the hand-held phototherapy device enabling operation of the phototherapy device according to one or more conditional prescription parameters originating at a remote computing device; activate the phototherapy light source; and transmit a second signal to a server; a server configured to: perform analysis of patient records, prescribed treatment protocols, and outcomes over populations of patients; perform computational analysis; determine an initial phototherapy dose based on a skin type or susceptibility to erythema of a user; and determine subsequent phototherapy doses using image analysis of an image of a treated area of skin and surrounding skin tissue, the analysis comprising an analysis of a degree of erythema of the treated area of skin or the surrounding tissue; a database communicatively connected to the server, the database storing patient records and prescribed treatment protocols; and a remote computing device configured to communicate with the server, the remote computing device comprising a processor and a memory, the remote computing device configured to: display a graphic user interface allowing a health care provider to enter the one or more conditional prescription parameters; transmit a first communication to the server; and receive a second communication from the server.

In a fifth broad embodiment, the present disclosure provides use of a system for treating a skin condition, the condition comprising psoriasis, vitiligo, or eczema, with phototherapy, the system comprising a hand-held phototherapy device comprising a light emitting diode (LED) phototherapy light source configured to emit a light comprising a UVB wavelength in the range of 300-320 nm and a signal receiver; and a patient computing device comprising a smartphone, the smartphone comprising a processor and a memory, the smartphone configured to: present an interface providing a treatment schedule, treatment reminders, and directions for how to use the phototherapy device; transmit a first signal to the hand-held phototherapy device enabling operation of the phototherapy device according to one or more conditional prescription parameters originating at a remote computing device; activate the phototherapy light source; and transmit a second signal to a server; a server configured to: perform analysis of patient records, prescribed treatment protocols, and outcomes over populations of patients; perform computational analysis; determine an initial phototherapy dose based on a skin type or susceptibility to erythema of a user; and determine subsequent phototherapy doses using image analysis of an image of a treated area of skin and surrounding skin tissue, the analysis comprising an analysis of a degree of erythema of the treated area of skin or the surrounding tissue; a database communicatively connected to the server, the database storing patient records and prescribed treatment protocols; and a remote computing device configured to communicate with the server, the remote computing device comprising a processor and a memory, the remote computing device configured to: display a graphic user interface allowing a health care provider to enter the one or more conditional prescription parameters; transmit a first communication to the server; and receive a second communication from the server.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The FIGURE is a flow-chart showing a non-limiting example of a system for treating a skin condition with phototherapy according to the present disclosure. In the FIGURE, dashed arrows represent signals or communications that are sent and/or received according to systems according to some embodiments of the present disclosure. Elements bounded in dashed lines represent elements of systems of the present disclosure that are present in some embodiments of systems of the present disclosure.

DETAILED DESCRIPTION

Described herein are systems and methods for treating skin conditions. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein, "skin condition" means any skin condition, disease, or disorder, which may be treated with phototherapy. "Skin condition" includes, without limitation, psoriasis, eczema, and vitiligo.

As used herein, "affected area" means any skin area that is affected by a skin condition. "Affected area" includes, without limitation, skin lesions, areas of scaly skin, areas of discolored skin, rashes, irritations, and skin areas of discomfort, each associated with or caused by a skin condition.

As used herein, "processor" means any computer processor, for example and without limitation, a CPU.

As used herein, "computer-readable storage medium" means any storage medium suitable for reading by a computer, for example and without limitation a RAM.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Treatment of Skin Conditions by Phototherapy

Described herein are systems and methods for treating affected areas associated with skin conditions with phototherapy. Non-limiting examples of affected areas include skin lesions, rashes, irritations, scaliness, discoloration or discomfort caused by one or more or psoriasis, eczema, or vitiligo. Generally, systems described herein for treating skin conditions with phototherapy comprise a phototherapy device, a patient computing device, and a server.

Skin conditions such as psoriasis, vitiligo, and eczema may be treated by administration of light radiation, such as UV radiation, to the affected area, also referred to as phototherapy. UVB radiation having a wavelength in the range of 300-320 nm is effective in treating certain skin conditions including psoriasis, vitiligo, and eczema. Generally, by applying a dose of UV radiation measured by both radiation intensity and time of exposure, a physician attempts to apply the maximum dosage possible to the area affected by the skin condition without burning the surrounding skin tissue. If the physician observes excessive redness or erythema in the surrounding skin tissue after treatment, she may recommend or prescribe a reduction in the dose. By contrast, if there is no redness or erythema observed, she may recommend or prescribe an increase in the dose.

Traditionally, in order for skin condition patients, for example psoriasis, vitiligo and/or eczema patients, to undergo UV phototherapy, those patients have often been required to attend at a clinician's office, such that the prescribing clinician could be present to administer and/or supervise the treatment, and to observe the effects, for example erythema as discussed above, and adjust the prescribed phototherapy dose accordingly. Additionally, traditional phototherapy treatment protocols require office visits three days per week for many weeks, which is inconvenient for patients, especially patients with traditional work schedules. As a result of these inconveniences, patients suffering from such skin conditions often fail to complete or comply with traditional office based phototherapy regimens.

The advent of home phototherapy has led to the development of equipment that allows the patient to receive phototherapy treatment at a convenient time in the comfort of their home. While these options appear to solve convenience issues, they introduce physician concerns regarding adherence to protocols and follow-up. Physicians are reluctant to prescribe home phototherapy systems that rely on the patient for dose control and schedule without monitoring.

Use of Certain Systems and Methods for Treating Skin Conditions in Patients with Phototherapy Systems and methods described herein address certain of these problems. In use, according to some embodiments, a hand-held phototherapy device as described herein is operable by a skin condition patient at her convenience in her own home or some other suitable place. A prescribing physician may evaluate a patient's skin condition, for example by observing skin affected by psoriasis, vitiligo, or eczema, and prescribe conditional prescription parameters for phototherapy treatment. The prescribed parameters may comprise a standardized, known and established phototherapy regimen, may be customized based on a physician designed, or may be a semi-customized standardized regimen that is adjusted by the physician based on the patient's needs and/or response to treatment. In some embodiments, the system described herein will deliver the same level of control as phototherapy administered within a clinical setting by delivering the prescribed doses in accordance with the protocol and providing records of all treatments.

As discussed in further detail below, by use of certain systems and methods described herein, the prescribing physician may exercise some control over the home use of the phototherapy device by the patient. In some embodiments, conditional prescription parameters, for example number and location of treatment sites, initial dose, method to determine subsequent doses, method to determine adjustments for missed days, maintenance treatment doses, treatment assessment method, treatment assessment frequency, treatment parameters in case the patient computing device is unavailable, enablement of the treatment dependent on completion of office visits or consults, enablement of the device dependent on acknowledgement of physician supplied materials, enablement of the device dependent on fulfillment of other physician requests such as user supplied photos, conditions in which the treatment would be disabled, are entered by the physician either directly into a patient computing device to be used or operated by the patient, or into a remote computing device to be used or operated by the physician. This information is then communicated, in some embodiments, from the remote computing device to a server. In turn, this information is then communicated to a patient computing device which, in some embodiments, is to be used or operated by the patient. The patient computing device is configured to transmit a first signal to the phototherapy device, as discussed more fully below, enabling operation of the phototherapy device according to the conditional prescription parameters (e.g. intensity, time, or frequency), activate the phototherapy light source, and transmit a second signal to a server, reporting activation of the phototherapy device.

In some embodiments, the patient inputs information, for example whether and when a treatment has been completed, the degree of redness or erythema observed at the treatment site, size or location of an affected area, disease state, and/or any other observations or notes the patient may have or may be required or requested by the prescribing physician, into the patient computing device. In some embodiments, this patient information is then communicated to the prescribing physician.

In some embodiments, the patient computing device is configured to direct the patient as to how to carry out the phototherapy treatment. In some embodiments, a global positioning system (GPS)-style interface facilitates the patient's navigation through the treatment, which may be based on information inputted into either a remote computing system or directly to the patient-operated computing system itself by the prescribing physician. In some embodiments, the patient computing device prompts the patient/user through a series of commands as to how to operate the phototherapy device in order to carry out the treatment regimen. In some embodiments, the patient computing device prompts the patient, by way of reminders, that it is time to carry out a scheduled treatment regimen.

Components of Certain Systems and Methods Described Herein

Phototherapy devices of the present invention comprise a housing comprising control circuitry as well as a phototherapy light source. In an embodiment, the phototherapy device is hand-held. In an embodiment, the light source comprises one or more light-emitting diodes (LEDs). When activated, the light source emits a light comprising UVB radiation. In an embodiment, the UVB radiation comprises a wavelength in the range of 300-320 nm. It should be understood that radiation in other therapeutic wavelengths may be emitted as well including, for example, radiation in the UVA range. It should also be understood that other light sources besides LEDs are suitable for use with the systems and methods described herein.

In an embodiment, the phototherapy device comprises a processor configured to run software and an application. In an embodiment, the phototherapy device comprises a display screen for displaying a graphic user interface. In an embodiment, the phototherapy device comprises a processor with a timer that adjusts the duration of the treatment in order to control the dose with a fixed power supplied to the light source. In another embodiment, the power supplied to the light source is adjusted, thereby controlling the intensity of the light emitted therefrom.

The phototherapy device comprises a signal receiver for receiving a signal from a signal transmitter in the patient computing device. Any signals described herein are, depending upon the embodiment, wireless, or non-wireless, signals. Any transmitters or receivers described herein are, depending on the embodiment, for transmitting and/or receiving wireless signals, or for transmitting and/or receiving non-wireless signals.

In an embodiment, the phototherapy device is configured to communicate with the patient computing device. In some embodiments, the patient computing device is physically incorporated with the phototherapy device, such as by being housed in a common housing. In an embodiment, the patient computing device is configured to be connected to the phototherapy device by a physical connection, such as a wire or other connection for transmitting signals between the phototherapy device and the patient computing device. In another embodiment, the patient computing device is configured to send and/or receive wireless signals to and/or from the phototherapy device. In an embodiment, the wireless signals are transmitted via near-field, Bluetooth™, infrared, radio, or another suitable wireless technology. In an embodiment, the patient computing device is a mobile telephone device, for example a smartphone. In another embodiment, the patient computing device is a home computer or laptop computer. In another embodiment, the patient computing device is a tablet device.

In an embodiment, the patient computing device comprises a first processor. In a further embodiment, the patient computing device comprises a first display, coupled to the first processor, and a signal transmitter coupled to the first processor. In a still further embodiment, the patient computing device comprises a first non-transitory computer-readable medium encoded with a first computer program including a first set of instructions executable by the first processor. When executed, by the first processor, the first set of instructions causes the first processor to: display a first GUI on the first display; transmit a first signal to the signal receiver on the phototherapy device, thus enabling operation of the phototherapy device; activate the phototherapy light source; and transmit a second signal.

Use of the Described Systems According to Some Embodiments

In use, systems according to some embodiments permit a user to either passively or actively transmit a signal from the patient computing device, for example a smartphone, to the phototherapy device. In some embodiments, the signal enables operation of the phototherapy device, for example allowing activation of the phototherapy light source. In some embodiments, the parameters of this operation, for example the duration and/or intensity of the phototherapy treatment, may be determined by the signal transmitted by the patient computing device to the phototherapy device.

In an embodiment, the system further comprises a server, which is configured to communicate with the patient computing device, and to receive a second signal therefrom. In an embodiment, the server comprises a database of patient records and prescribed treatment protocols, comprising prescription parameters. In an embodiment, the server stores patient information and/or patient records about a patient receiving or scheduled to receive phototherapy treatment. In an embodiment, the patient records comprise one or more of the following: treatment dates and times, treatment durations, applied treatment energies, treatment site photos, analysis of treatments site photos, patient/physician correspondence, assessments of treatment sites, and changes to the treatment protocol.

In an embodiment, the server is configured to perform analysis of patient records, prescribed treatment protocols, and outcomes over populations of patients. In an embodiment, the server is configured to perform computational analysis. In an embodiment, the computation analysis is an analysis of degree of erythema of a treated area of skin and surrounding skin tissue. In another embodiment, the computational analysis comprises an analysis of treatment progression comprising size and severity of disease.

In use, according to some embodiments, a user inputs patient information into the patient computing device, for example by use of a smartphone app. The patient information may be manually inputted by the patient, for example by selecting options from menus, by typing in notes, or by taking a photograph of a treated area and uploading that photograph into the patient computing device. In an embodiment, the patient computing device is configured to present an interface that allows the patient to capture an image of a treated area of skin and surrounding skin tissue. In an embodiment, the patient computing device comprises a camera for capturing such an image.

In an embodiment, the remote computing device is configured to present an interface that provides guidance to the patient for operation of the phototherapy device. In certain embodiments, the remote computing device is configured to present an interface providing a treatment schedule, treatment reminders, and/or directions for how to use the phototherapy device.

In an embodiment, the phototherapy system includes a second computing device that is a remote computing device. The remote computing device is configured to communicate with the server, and comprises a processor and a memory. The remote computing device is configured to present a graphic user interface, allowing a physician or other health care provider to set one or more conditional prescription parameters, review information pertaining to operation of the phototherapy device, and adjust the conditional prescription parameters, to transmit a first communication to the server, and to receive a second communication from the server. In an embodiment, the first communication is transmitted from the server to the patient computing device.

In an embodiment, the server is configured to determine an initial phototherapy dose for treatment, based on the user's skin type, or susceptibility to erythema of the user or patient. For instance, where patients are known to have a skin type that is generally associated with susceptibility to erythema, or if it is known that an individual patient is susceptible to erythema when exposed to UVB radiation, the initial phototherapy dose determined is lower than where patients are known to be relatively unsusceptible to erythema.

In use, in an embodiment, the remote computing device is operated by a prescribing physician or an assistant of the prescribing physician, or some other health care professional. In some embodiments, the prescribing physician uses the remote computing device to review patient information displayed in a GUI. In some embodiments, the prescribing physician runs an application on the remote computing device to facilitate interaction with the patient information, and/or to monitor treatment progression, and/or to adjust the treatment parameters.

Computing Device

In some embodiments, the system and method described herein include a computing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

Non-Transitory Computer Readable Storage Medium

In some embodiments, the system and method disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the system and method disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the system and method disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the system and method disclosed herein include one or more databases, or use of the same. In view of the disclosure provided herein, those of skill in the art will recognize that many databases are suitable for storage and retrieval of patient information. In various embodiments, suitable databases include, by way of non-limiting examples, relational databases, non-relational databases, object oriented databases, object databases, entity-relationship model databases, associative databases, and XML, databases. In some embodiments, a database is internet-based. In further embodiments, a database is web-based. In still further embodiments, a database is cloud computing-based. In other embodiments, a database is based on one or more local computer storage devices.

EXAMPLES

The following illustrative examples are representative of embodiments of the software applications, systems, and methods described herein and are not meant to be limiting in any way.

Example 1

Jane is diagnosed with a mild case of psoriasis on her elbows and right leg. Her doctor discusses the treatment options with her and together they determine that targeted home phototherapy is the right treatment for her. After meeting with her physician, she is provided with a box containing a hand-held phototherapy device, and instructed that her prescription will be filled at the office and automatically populated into the device via her mobile phone. She is also instructed to download the Skylit Phototherapy App on her mobile phone, in order to interface with the device and the physician.

The physician launches the Skylit Phototherapy Portal, a web based software application, on her office computer. She enters Jane's patient information, including her skin type, lesion sizes and locations, and selects a treatment protocol from a list of options. The protocol indicates the initial dose that the physician is prescribing and the dose adjustment method. The physician also attaches patient information that will be downloaded to Jane. Since this is Jane's first experience with phototherapy, the physician submits a few post-treatment questions for Jane to answer and requests photos of the treatment sites. The physician also requests an office visit after the first two weeks of treatment.

Jane returns home and opens the box. The phototherapy device consists of a small handheld device with a charging cable. Also included in the box is a set of UV protection goggles. She plugs the device into the charging cable and proceeds to download the Skylit Phototherapy App onto her mobile phone. Jane runs the Skylit Phototherapy App and she notes that her treatment regimen is already loaded. She reads the patient information that the physician provides, and acknowledges having received the information. The Phototherapy App shows the schedule including treatment days, assessment days, office visits and information requests. Jane reviews the schedule and notes that her first therapy sequence is scheduled for the next day.

The next morning, Jane's phone displays a reminder that her therapy is due to be completed that day. She decides to proceed with the therapy and requests initiation of the therapy from within the Phototherapy App. The App indicates that she will be receiving a sequence of 4 treatments consisting of right elbow, left elbow and two adjacent treatments on the right leg. She is informed about the dose and approximate time that each treatment in the sequence will last. The phototherapy sequence is sent to the device, and she listens to an audio confirmation that her device is enabled. Her phone enters into navigation mode and provides audio and visual indications guiding the treatment sequence in a manner similar to a GPS navigation system.

Jane picks up the handheld phototherapy device and notes that the display also indicates the site, time, and dose of the first treatment. She puts on her UV protection goggles, places the device on her right elbow and presses the start button. The device glows a cool blue color as the treatment is administered. At the conclusion of the first treatment she hears an audible sequence of tones from the device and the navigation system on her phone indicates that the first treatment is completed successfully.

The phototherapy navigation system on the phone directs Jane to apply the device to her left elbow and to actuate the second treatment. Jane places the device on her left elbow, presses the start button, and completes the second therapy. The phototherapy navigation system on the phone indicates that the next two therapies are adjacent therapies that will take two treatments to cover the area. Jane is directed to apply the device to the first area and press the start button. After completion of the first area, the navigation system directs her to apply the therapy to the adjacent site and to press the start button. After completion of the therapy sequence, the device indicates that the therapy sequence has been successfully completed. Jane removes the device from the treatment area and powers the device down. She plugs the device into the charging cable and returns to her phone.

The Skylit Phototherapy App indicates that the treatment sequence is successfully completed and prompts her to answer a few questions from her physician about her first treatment. Jane answers the questions and adds a note to the physician that the treatment was simple and went well. The Skylit Phototherapy App shows the updated schedule of phototherapy events and indicates that the next scheduled activity is a color assessment planned for the next day. On the following day, Jane's phone reminds her that she needs to complete a color assessment of her treatments. At her convenience, she launches the Skylit Phototherapy App and is asked to assess the redness color (no redness, pink, red) of each treatment site. She is informed that this assessment is to be used to make an adjustment in her treatment. Jane completes the assessment and the Phototherapy App indicates that her physician requests a photo of the treatment sites. Using the camera included in her mobile phone, Jane takes a photo of each treatment site and the photos are automatically uploaded to her patient file.

On the next treatment day, Jane receives a reminder from her phone that her next treatment is ready. At her convenience, Jane launches the Skylit Phototherapy App and proceeds. The Phototherapy App indicates that her treatment dose has been increased for her right elbow and left elbow, since there is no sign of redness, but the treatment dose will remain the same for her right leg. She is informed that her treatment sequence is enabled and the approximate duration of each treatment. Jane unplugs the phototherapy device from the charging cable and puts on her UV goggles. The display indicates the information for the first therapy and her phone enters navigation mode to guide her through the sequence. She completes the treatment sequence in the same manner as previously. Jane's physician decides to check up on her and gain access to her patient file using the Skylit Phototherapy Portal on her office computer. She notes that Jane has successfully completed two treatments and indicates that everything is going well. She leaves a note for Jane to continue with the treatments and contact her if there are any issues.

Example 2

Mary has been recently diagnosed with a mild case of psoriasis on her scalp. Her doctor discusses the treatment options with her and together they determine that targeted home phototherapy is an appropriate treatment for her. Mary does not own a smartphone, but is comfortable using her computer to download therapy sequences, so she and her doctor agree that this will be the best method for her to use to control the administration of her treatments.

After meeting with her physician, she is provided with a box containing a hand-held phototherapy device and is instructed that her prescription will be filled at the office and available for downloading by her computer. Her physician launches the Skylit Phototherapy Portal, a web based software application, on her office computer. She enters Mary's information, including her skin type, and selects a protocol from a list of options. The protocol indicates the initial dose that the physician is prescribing and the dose adjustment method. The physician also attaches patient information that will be downloaded to Mary. Since this will be Mary's first experience with phototherapy, the physician submits a few post-treatment questions for Mary to answer. The physician also requests an office visit after the first two weeks of treatment.

Mary returns home and opens the box. The phototherapy device consists of a small handheld device with a USB cable. Also included in the box is a set of UV protection goggles. She plugs the device into her computer using the USB cable. Mary runs the Skylit Phototherapy App from her web browser and she notes that her treatment regimen has already been loaded into the system. She reads the patient information that the physician has provided and acknowledges that she has received the information. The Phototherapy App shows the schedule, including treatment days, assessment days, office visits and information requests. Mary reviews the schedule and notes that her first therapy sequence is scheduled for tomorrow.

The next morning, Mary receives an e-mail reminding her that her therapy is ready. She proceeds with the therapy. She launches the Phototherapy App from her browser and notes that the App indicates she will be receiving a sequence of six treatments for her scalp. She is informed about the dose and approximate time that each treatment in the sequence will last. She is also informed that there will be multiple adjacent treatments on the scalp, so she will be placing the device in adjacent areas and rotating the device several times prior to treatment to displace the hair in the scalp area. The phototherapy sequence is sent to the device and she hears an audio confirmation that her device is enabled.

Mary disconnects the phototherapy device from the USB cable and brings the device into the TV room to complete her therapy. She notes that the display indicates the site, time and dose of her first treatment. She attaches the scalp accessory over the optical end of the device and puts on her UV protection goggles. Mary places the device on the leftmost area, rotates the device a few times to minimize hair blocking the treatment and then presses the start button. At the conclusion of the first treatment she hears an audible sequence of tones from the device.

Mary removes the device from the treatment area and views the display. The display indicates the first therapy has completed successfully and the second is ready. Mary places the device adjacent the first treatment area and rotates the device a few times. She presses the start button to initiate the second treatment. Mary repeats the process to complete all of the treatments in the sequence. The device indicates that the treatment sequence is successfully completed.

Mary removes the device from the treatment area and powers the device down. She returns to the computer, plugs the device back in to the USB port and returns her focus to the computer screen. When she plugs the device into the computer, the Skylit Phototherapy App uploads the treatment records and indicates that the treatment sequence has successfully completed. She is also prompted to answer a few questions from her physician about her first treatment. Mary answers the questions and decides to add a note to the physician that the treatment has gone well. The Skylit Phototherapy App shows the updated schedule of phototherapy events and indicates that the next scheduled activity is a color assessment planned for the next day.

On the following day, Mary receives an e-mail reminder that she needs to complete a color assessment of her treatments. At her convenience, she launches the Skylit Phototherapy App and is asked to assess the redness color (no redness, pink, red) of her scalp. She is informed that this assessment will be used to make an adjustment in her treatment. Mary uses a hand mirror and the bathroom mirrors to view the treatment area and complete the assessment.

On the next treatment day, Mary receives an e-mail reminder that her treatment is ready. At her convenience, she launches the Skylit Phototherapy App. The Phototherapy App indicates that her treatment dose has been increased since there is no sign of redness. She is informed that her treatment sequence is enabled, and the approximate duration of each treatment. Mary removes the device from the USB cable and moves to the TV room to complete her therapy. After completing the treatment sequence, Mary plugs the device back into the computer. The Phototherapy App indicates that the treatment has been successful. Mary's physician decides to check up on her, and gains access to her patient records using the Skylit Phototherapy Portal on her office computer. She notes that Mary has successfully completed two treatment sequences and indicates that everything is going well. She leaves a note for Mary to continue with the treatments and to contact her if there are any issues.

Example 3

Dale has been recently diagnosed with a mild case of eczema on the back of both legs and on both thighs. His doctor discusses the treatment options with him and together they determine that targeted home phototherapy is an appropriate treatment for him. Dale is not comfortable utilizing technology to drive his treatments, so his physician decides to prescribe a fixed treatment sequence to be programmed into the device at the physician's office.

The physician launches the Skylit Phototherapy Portal, a web based software application on his office computer. He enters Dale's information and selects a protocol from among the options. The physician modifies the protocol settings by selecting an option to prescribe a treatment sequence download. This option disables the dose adjustment feature. He enters a prescription for six treatment sequences to be delivered on each Monday, Wednesday and Friday over the following two weeks. He also selects an option to have the device programmed in the office.

The physician provides Dale with patient information and schedules a follow up appointment after the first two weeks. He informs Dale that a clinician will program the device and show him how to use it. The clinician enters the room with a box containing his phototherapy device. He opens the box and removes the device. The clinician shows Dale how to use the device and answers Dale's questions. The clinician launches the Skylit Phototherapy App on his tablet and downloads the therapy sequences to the device.

Dale returns home with the device and plugs the device into a wall plug USB charger. The next morning, Dale picks up the device and powers it on. The device indicates that the therapy sequence is ready for him. He decides to continue with the treatment sequence. After reminding him to wear safety goggles, the device indicates that he has a sequence of eight treatments. After acknowledging, he notes that the display indicates the site, time and dose of the first treatment. He puts on his UV protection goggles, places the device on the first treatment site and presses the start button.

The device glows a cool blue color as the treatment is administered. At the conclusion of the first treatment he hears an audible sequence of tones and notices that the blue light has turned off. The device display then indicates the site, time, and dose of the second treatment. He places the device over the second treatment site and completes the second therapy. Dale repeats the process for all eight treatment sites. After completion of the therapy sequence, Dale removes the device from the treatment area. He notices that the device display indicates that the therapy sequence has been successfully completed.

Dale powers the device down and plugs the device into the USB cable to charge in a wall plug. The next day, Dale returns to the device and powers it on. The device indicates that treatment is scheduled for the next day. Dale returns the following day and proceeds through the treatment sequence without any problems. He completes the treatment sequence on the scheduled days for the following two weeks in accordance with the physician's prescription.

After two weeks of treatment, Dale returns to the clinic for his appointment with the physician to discuss the treatment. The physician asks if Dale's skin has experienced any change in color after the treatments and examines the progress of the treatment. Dale indicates that he has not had any issues with the treatment and had not noticed any redness. Based on this information, the physician indicates that he will increase the dose of the treatment and set Dale up with another two weeks of treatment. He also informs Dale that the clinician will be able to make adjustments to the therapy thenceforth. The clinician enters the adjustments to the protocol in the Skylit Phototherapy App and proceeds to program the device.

Dale returns home and continues to use the device to treat his eczema in accordance with the prescription. At the end of the two weeks, he meets with the clinician to renew his treatment. Dale indicates that one of the sites (back of the left leg) has cleared and one of the sites (right thigh) is pink from the treatment. The clinician indicates that the treatment will be extended for another two weeks with a couple of modifications. The left leg treatment will be eliminated since clearance has been achieved. Also, the dose will be increased on all of the remaining sites except for the right thigh since that site is pink from the treatment. The next appointment with the clinician is scheduled for two weeks later.

While preferred embodiments of the present subject matter have been shown and described herein, it will be obvious to those skilled in the art that such embodiments are provided by way of example only. Numerous variations, changes, and substitutions will now occur to those skilled in the art without departing from the described subject matter. It should be understood that various alternatives to the embodiments of the subject matter described herein may be employed in practicing the subject matter described herein. It is intended that the following claims define the scope of the subject matter described herein and that methods and structures within the scope of these claims and their equivalents be covered thereby.

What is claimed is:

1. A system for self-administration of phototherapy, the system comprising:
    a) a server;
    b) a phototherapy device comprising a phototherapy light source;
    c) a mobile computing device comprising a processor, a memory, a transmitter, and a receiver; and
    d) a remote computing device, which is remote from the mobile computing device, comprising a processor, a memory, and a graphic user interface;
wherein the server communicates wirelessly with the mobile computing device and communicates with the remote computing device;
wherein the mobile computing device communicates with the phototherapy device;
wherein the remote computing device presents the graphic user interface allowing an operator to set or adjust one or more conditional prescription parameters, and transmits a first communication comprising the one or more conditional parameters to the server;
wherein the mobile computing device receives the first communication from the server;
wherein the mobile computing device sends a first signal to the phototherapy device permitting a patient to initiate phototherapy by the phototherapy device according to the one or more conditional prescription parameters;
wherein the phototherapy device generates a second signal reporting operation of the phototherapy device and transmits the second signal to the mobile computing device, wherein the mobile computing device sends a third signal, reporting operation of the phototherapy device, to the server upon or subsequent to receipt of the second signal reporting operation of the phototherapy device; and
wherein the remote computing device receives a second communication from the server subsequent to receipt of the third signal by the server, the second communication reporting operation of the phototherapy device by the patient.

2. The system of claim 1, wherein the one or more conditional prescription parameters comprise: number and location of treatment sites, initial dose, method to determine subsequent doses, method to determine adjustments for missed days, maintenance treatment dose, treatment assessment method, treatment assessment frequency, treatment parameters in case the remote computing device is unavailable, enablement of the treatment dependent on completion of office visits or consults, enablement of the phototherapy device dependent on acknowledgement of physician supplied materials, enablement of the phototherapy device dependent on fulfillment of requests such as user supplied photos, conditions in which the treatment would be disabled, or any combination thereof.

3. The system of claim 1, wherein the server comprises a database of patient records and prescribed treatment protocols comprising conditional prescription parameters.

4. The system of claim 3, wherein the patient records comprise: treatment dates and times, treatment durations, applied treatment energies, treatment site photos, analysis of treatments site photos, patient/physician correspondence, assessments of treatment sites, changes to the treatment protocol, or any combination thereof.

5. The system of claim 1, wherein the server is further configured to perform analysis of patient records, prescribed treatment protocols, and outcomes over populations of patients.

6. The system of claim 1, wherein the server is further configured to perform computational analysis.

7. The system of claim 6, wherein the computational analysis comprises analysis of degree of erythema of a treated area of skin and surrounding skin tissue.

8. The system of claim 1, wherein the server is further configured to determine an initial phototherapy dose based on a user skin type or susceptibility to erythema of a user of the phototherapy device.

9. The system of claim 1, wherein the phototherapy device comprises a hand-held phototherapy device.

10. The system of claim 1, wherein the phototherapy light source is configured to emit a light comprising a UVB wavelength in the range of 300-320 nm.

11. The system of claim 10, wherein the phototherapy light source comprises a light emitting diode (LED).

12. The system of claim 1, wherein the mobile computing device comprises a smartphone, the signals comprise wireless signals, the transmitter comprises a wireless transmitter, and the receiver comprises a wireless receiver.

13. The system of claim 1, wherein the mobile computing device is further configured to present an interface allowing the patient to capture an image of a treated area of skin and the surrounding skin tissue.

14. The system of claim 1, wherein the mobile computing device is further configured to present an interface providing guidance to the patient for operation of the phototherapy device.

15. The system of claim 1, wherein the mobile computing device is further configured to present an interface providing a treatment schedule, treatment reminders, directions for how to use the phototherapy device, or any combination thereof.

* * * * *